United States Patent [19]

Cullo et al.

[11] Patent Number: 4,623,530

[45] Date of Patent: Nov. 18, 1986

[54] CRYSTALLINE MAGNESIA-SILICA COMPOSITES AND PROCESS FOR PRODUCING SAME

[75] Inventors: Leonard A. Cullo, Hempfield Township, Westmoreland County; Edward F. Restelli, Jr., Oakmont Borough, Allegheny County; Francis J. Shiring, III, Hampton Township, Allegheny County, all of Pa.

[73] Assignee: United States Steel Corporation, Pittsburgh, Pa.

[21] Appl. No.: 703,568

[22] Filed: Feb. 20, 1985

[51] Int. Cl.⁴ .................... C01B 33/24; C01B 33/28; B01J 21/08; C07C 2/68

[52] U.S. Cl. ................................ 423/331; 423/328; 585/467; 502/251

[58] Field of Search .................. 423/331, 332, 328 T; 252/521; 502/251

[56] References Cited

U.S. PATENT DOCUMENTS

| | | | |
|---|---|---|---|
| 3,941,871 | 3/1976 | Dwyer et al. | 423/328 T |
| 4,283,306 | 8/1981 | Herkes | 423/328 T |
| 4,499,320 | 2/1985 | Garces | 423/328 |

Primary Examiner—Gary P. Straub
Attorney, Agent, or Firm—William L. Krayer

[57] ABSTRACT

Novel aromatic alkylation catalysts are manufactured by an extended hydrothermal treatment of the precipitation product of a magnesium salt with sodium silicate in the presence of tetrapropylammonium bormide or related compound.

8 Claims, 4 Drawing Figures

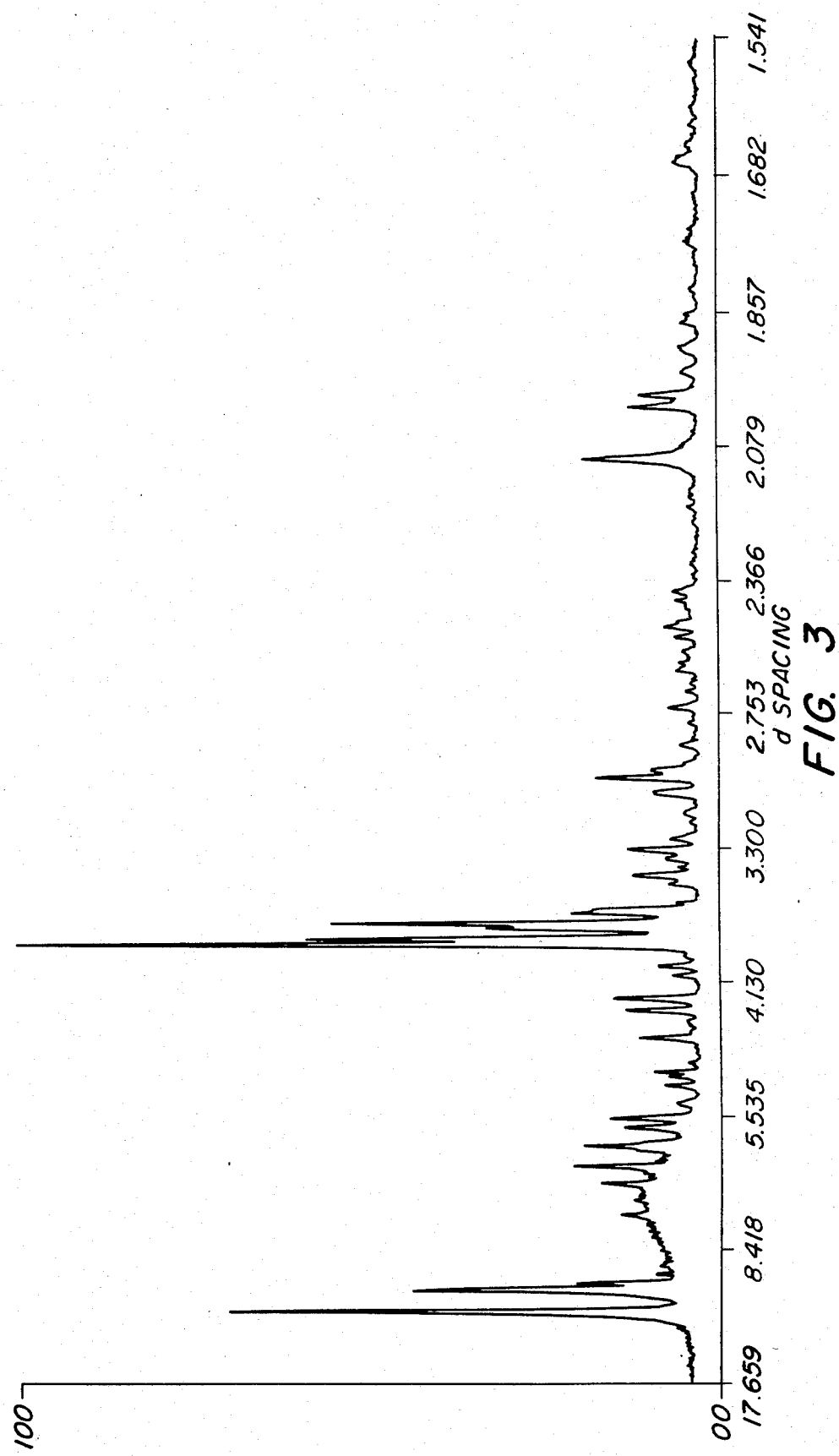

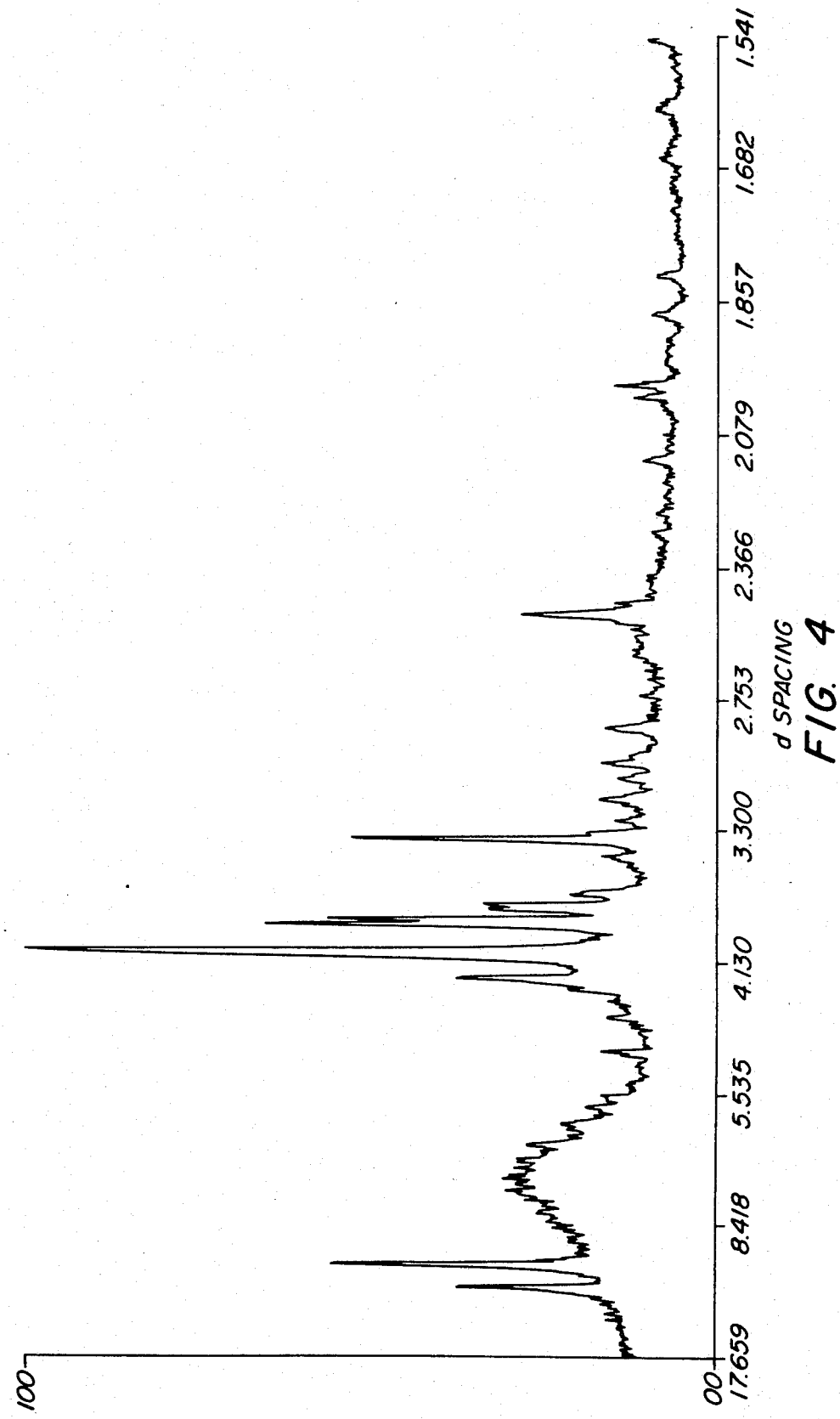

CRYSTALLINE MAGNESIA-SILICA COMPOSITES AND PROCESS FOR PRODUCING SAME

BACKGROUND OF THE INVENTION

In the past several years, much research has been conducted in the manufacture, composition, and use of crystalline shape-selective catalysts and molecular sieves, and the patent literature reflects both the economic significance of this area of research and the technical value of the prolific but apparently small increments of progress heretofore. Much of the work has concentrated on refinements of Silicalite and aluminosilicates.

Crystalline aluminosilicate "molecular sieves" can be described as rigid three dimensional networks primarily of tetrahedra of $SiO_4$ and $AlO_4$ in which the silicon and aluminum atoms are cross-linked by the sharing of oxygen atoms.

The basic configuration of silicon and oxygen atoms in a pure Silicalite composition is at least theoretically a lattice of tetrahedra. With the introduction of aluminum atoms to replace some of the silicon atoms, the tetrahedra containing them are considered to have negative valences and, typically, a sodium atom is formed to balance a negatively charged tetrahedron. The sodium atom, however, is not believed to be an integral part of the tetrahedral lattice structure, and in any event is amenable to ion exchange.

Prior art developments have led to the creation of many synthetic crystalline materials which are generally similar to naturally-occurring zeolites such as faujasite and mordenite. Synthetic crystalline aluminosilicates which are the most common and are described in the patent literature and publications have been designated by letters or other convenient symbols. Examples of these are Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979) and others. Other examples in the ZSM series are described in U.S. Pat. Nos. 4,016,245, 4,046,859, 4,287,166, 4,397,827, 4,448,675 and many other patents of Mobil Oil Corporation. See the article entitled "Shape-Selective Reactions with Zeolite Catalysts"; particularly part IV by Warren W. Kaeding, L. Brewster Young, and Chin-Chiun Chu, Journal of Catalysis 89, 267–273 (1984), describing the alkylation of toluene with ethylene to produce p-ethyltoluene as typical of the literature on the use of such materials as ZSM-5 in alkylation techniques.

Also previously disclosed are crystalline silica composition materials which exhibit molecular sieve properties characteristic of a number of crystalline aluminosilicates, but which exhibit none of the ion exchange properties which are requisite for a zeolitic molecular sieve. Such materials, of which a paradigm is described in a Union Carbide patent (U.S. Pat. No. 4,061,724), have been called Silicalites and are characterized by a very low aluminum content. See also U.S. Pat. Nos. 4,285,922 and 4,397,827, and Flanigen et al in Nature, V. 271, Feb. 9, 1978, p. 512. The use of aluminum-free materials is extolled in U.S. Pat. Nos. 3,941,871, 4,088,605 and 4,462,971.

Other crystalline silicates exhibiting both molecular sieve properties and ion exchange characteristics consist of three dimensional networks of $SiO_4$ and $FeO_4$ tetrahedra—see U.S. Pat. No. 4,208,305.

Representative of the patent literature on the use of crystalline silica, aluminosilica and similar catalysts for alkylation of aromatics are U.S. Pat. Nos. 3,751,506, 3,755,483, 4,002,698, 4,034,053, 4,086,287, 4,104,319, 4,113,788, 4,117,026, 4,127,616, 4,128,592, 4,288,647, 4,371,714, 4,158,024 and 4,447,666.

In the prior art there are references to the "promotion" of crystalline silica catalysts by the addition to preformed crystalline silica of various agents such as arsenic oxide, phosphorous oxide, magnesium oxide, boron oxide, antimony oxide, amorphous silica, alkaline earth oxides, (see U.S. Pat. Nos. 4,208,305 and 4,288,649) alkali metal carbonates and mixtures and precursors of the foregoing. In all these past teachings (i.e., Herkes U.S. Pat. No. 4,283,306, Dwyer U.S. Pat. No. 3,941,871), the promoters are added by impregnation or extended contact of a preformed crystalline silica with a liquid medium containing the additive. These techniques are familiar to persons skilled in the art and are reminiscent of those employed (see U.S. Pat. No. 3,031,420) in producing hydrotreating catalysts wherein cobalt and molybdenum solutions have been impregnated on supports such as alumina, or reforming catalysts where platinum salts have been impregnated on appropriate supports. Other catalyst preparations in which supports such as silica, alumina, clays, etc., have been promoted with various metals by a variety of methods such as impregnation, ion exchange, vapor deposition, etc., are familiar to workers in the art.

The preparation of two separate solutions to mix for forming a precipitate to be crystallized is discussed in U.S. Pat. No. 4,117,026 (see example 21 for the post-addition of magnesium), and the technique is also employed in U.S. Pat. No. 4,462,971. This is not the same as the "composited" approach mentioned for the addition of "silica-magnesia" in column 7, lines 27–40 of U.S. Pat. No. 3,702,886.

Magnesium has been added to crystalline silicates by extended contact in the aqueous phase, or by multiple impregnation, or by various other approaches to modifying a preformed silica structure. See, for example, U.S. Pat. Nos. 3,972,832, 4,034,053, 4,113,788, 4,117,024, 4,128,592, 4,137,195, 4,158,024, 4,166,047, 4,275,256, 4,283,306, 4,367,359, 4,370,508, 4,371,714, 4,371,721, 4,379,027 and 4,477,585. As will be seen below, our crystalline magnesium silicates are made in an entirely different manner, the magnesium being incorporated into the crystalline structure during its formation rather than after. There is no need to speak of the magnesium we use as a "replacing" cation as do the authors of U.S. Pat. No. 4,046,859 (col. 6, line 52). See also U.S. Pat. No. 4,200,528, which describes an amorphous magnesium silicate. The magnesium in our composition cannot be removed by conventional ion exchange techniques.

Our crystalline magnesium silicates also differ from the prior art in that by our procedure we have formed specific reaction products with characteristic X-ray diffraction patterns.

SUMMARY OF THE INVENTION

Our invention relates to novel crystalline silica-magnesia compositions, methods for preparing the same, and their use in the selective alkylation of aromatics. More particularly, it relates to a novel crystalline silica-magnesia catalyst composition which exhibits molecular sieve properties. It differs from the prior art, among other criteria, in that it employs magnesium placed in the crystal structure in a particular manner. Our composition has a unique method of preparation, differences in crystalline structure as shown by XRD patterns, and is superior in performance for alkylation reactions as compared to commercially available silica-based materials. Although a number of workers in the art, as discussed above, have disclosed magnesium-containing crystalline silicate solid acid catalysts, the magnesium has been added to the silicate phase after crystallization, resulting in a relatively uneven distribution of discrete particles of magnesia. In our preparation the magnesium component is added to the original mixture before crystallization takes place, resulting in a relatively uniform incorporation of magnesium in the crystalline structure of the catalyst.

In the final form the catalyst composition of this invention in terms of moles of magnesium oxide per mole of silicon dioxide is (0.005–0.25) MgO:1.0 SiO$_2$. The preferred range of moles of magnesium oxide per mole of silicon dioxide is (0.025–0.15) MgO:1 SiO$_2$. While some impurities such as aluminum, boron and iron appear to be helpful in the mechanism of acid catalysis, we prefer not to add them specifically for that purpose. We have found that it is extremely difficult to manufacture such a composition, using generally available materials, without including at least a very small amount of aluminum, as is acknowledged in U.S. Pat. No. 4,061,724 (Col. 4 lines 17–40) with respect to the manufacture of Silicalite.

Our novel crystalline magnesium silicate materials have definite X-ray diffraction patterns which distinguish them from other crystalline silicates.

Our composition will be described and compared with reference to the accompanying drawings which depict the X-ray diffraction patterns of our material and others.

FIG. 3 is an X-ray diffraction pattern of S-115 with magnesium acetate added in the manner described below.

FIG. 4 is an X-ray diffraction pattern of the composition of our invention made by the process of Example 2.

The X-ray diffraction pattern of the crystalline magnesium silicate made by the procedure of Example 1 has the characteristic values shown in Table I after calcination in air at 580° C. for one hour.

The strongest lines (interplanar spacing) for the new crystalline magnesium silicate are designated as VS (70% or more of most intense peak), S (40–70% of most intense peak), M (20–39% of most intense peak), W (10–19% of most intense peak), VW (10% of most intense peak).

TABLE I

| Magnesium Silicate | | |
|---|---|---|
| d | I | Relative Intensity |
| 4.08 ± 0.07 | 100 | VS |
| 3.38 ± 0.05 | 53 | S |
| 10.08 ± 0.2 | 35 | M |
| 3.87 ± 0.07 | 21 | M |
| 2.48 ± 0.05 | 18 | W |
| 11.2 ± 0.2 | 18 | W |
| 3.83 ± 0.07 | 18 | W |

TABLE II

| d | Commercial Union Carbide Silicalite Relative Intensity | ZSM-5 Relative Intensity |
|---|---|---|
| 11.04 | VS | VS |
| 9.92 | S | VS |
| 4.07 | VW | |
| 3.83 | VS | VS |
| 3.78 | S | S |
| 3.38 | VW | |

As seen by comparison to Table II, the crystalline magnesium silicate X-ray diffraction pattern of this invention contrasts sharply with commercial Union Carbide Silicalite (crystalline silica) and ZSM-5 aluminosilicates.

Figure 1:
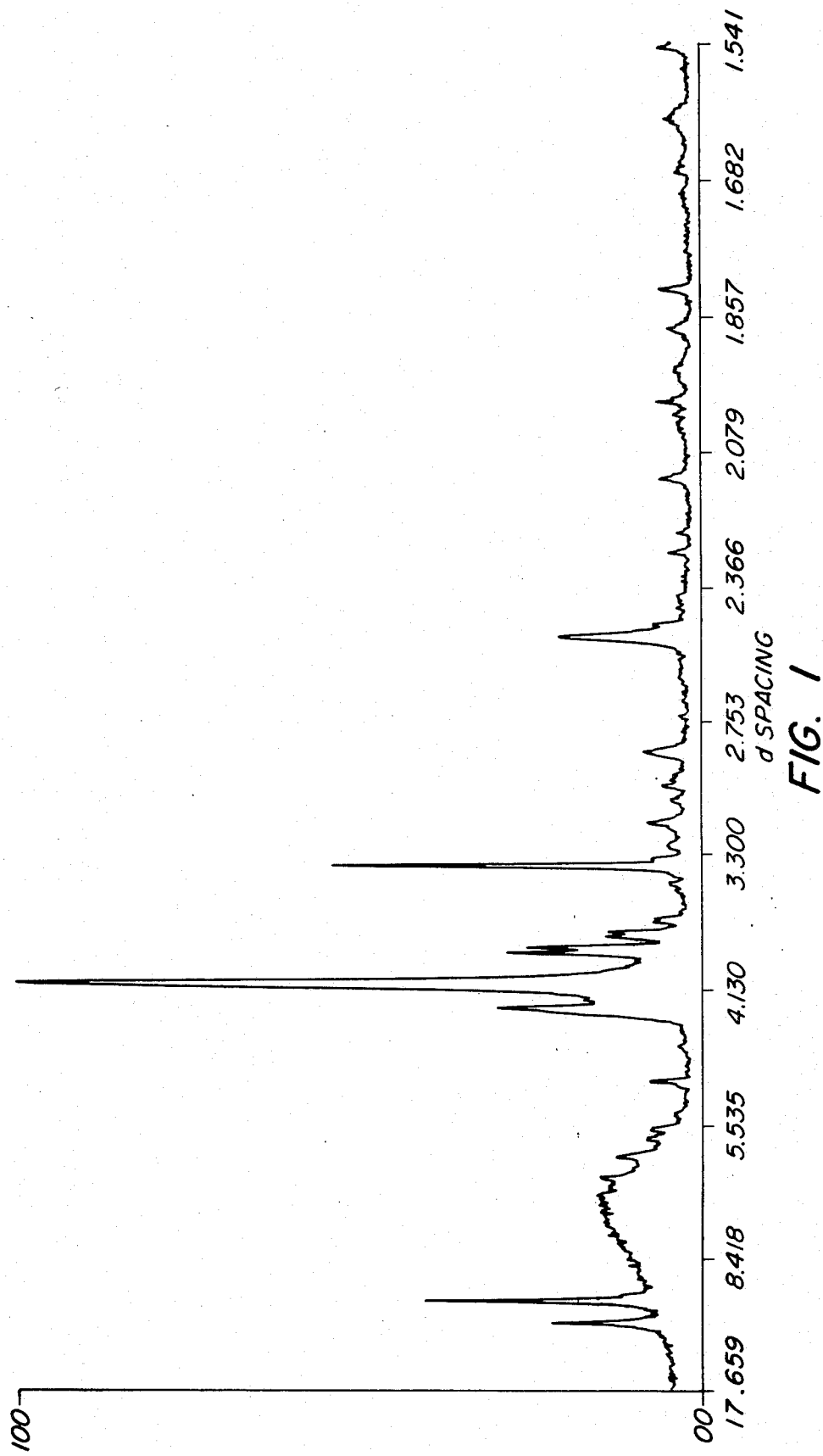
FIG. 1 is an X-ray diffraction pattern of a sample of our "magnesium silicate" composition made by the method recited in Example 1.

The preferred form of our crystalline magnesium silicate is defined by the X-ray diffraction pattern shown in FIG. 1 and listed in Table I. The most intense peak at a d spacing of 4.08 Å increases as the composition is maintained in the preferred range of MgO to SiO$_2$ of 0.025 to 0.15. Concurrently the line at 3.38 Å also increases as the composition is varied into the preferred range. The presence of these lines is clearly distinguishable from prior art silicates such as ZSM-5 and Silicalite. In silicates such as ZSM-5 and Silicalite, these main lines at d spacing 4.08 Å and 3.38 Å are very weak or non-existent. Additionally, the peak intensities in ZSM-5 and Silicalite X-ray diffraction patterns of d-spacing of 11.04 Å and 9.93 Å (see Table II) are generally found in the ratio of about 1.3–1.7 (d 11.04 Å/d 9.93 Å) and are reversed in our crystalline magnesium silicate (see FIG. 1) wherein the ratio is generally in the range of 0.4 to 0.6 (d 11.04 Å/d 9.93 Å).

The addition of magnesia by our method results in a novel crystalline material. The addition of magnesia to ZSM-5 and Silicalite of the prior art results in a mixture of ZSM-5 with a magnesia phase and Silicalite with a magnesia phase rather than incorporation to form a new material. Our invention is clearly distinguished from the prior art disclosures as we are forming a new material, a crystalline magnesium silicate, which has a definite characteristic X-ray diffraction pattern as shown in FIG. 1 and summarized in Table I. Our crystalline magnesium silicate differs sharply from the crystalline Silicalite X-ray pattern shown in FIG. 2 and the line spacing for ZSM-5 shown in Table II. In the prior art, crystalline silicas and ZSM-5 family of supports are promoted by addition of various agents through impregnation, physical admixture or extended contact; however, the fundamental support characteristics (X-ray patterns) are essentially unchanged. In U.S. Pat. No. Re. 29,948 a crystalline silicate is described in which a variety of metals have been added in the synthesis media—sodium, tin, calcium, or zinc. In this reference, column 4, lines 52–61, it is noted "Regardless of the synthesized form of the organosilicate, the spatial arrangement of atoms which form the basic crystal latices remain essentially unchanged by the described replacement of sodium or other alkali metals or by the presence in the initial reaction mixture of metals in addition to sodium as determined by an X-ray diffraction of the resulting organosilicate. The X-ray diffraction patterns of such products are essentially the same as set forth in Table I above."

U.S. Pat. No. Re. 29,948 (column 2, lines 38–60) goes on to describe its Table I as follows: "As above noted, the family of crystalline metal organosilicates disclosed and claimed herein have a definite X-ray diffraction pattern. Such X-ray diffraction pattern, similar to that for the ZSM-5 zeolites, shows the following significant lines":

The principal lines (Table I of U.S. Pat. No. Re. 29,948) presented are given below:

| Interplanar Spacing d (Å) | Relative Intensity |
|---|---|
| 11.1 | S |
| 10.0 | S |
| 3.85 | VS |
| 3.71 | S |

Figure 2:
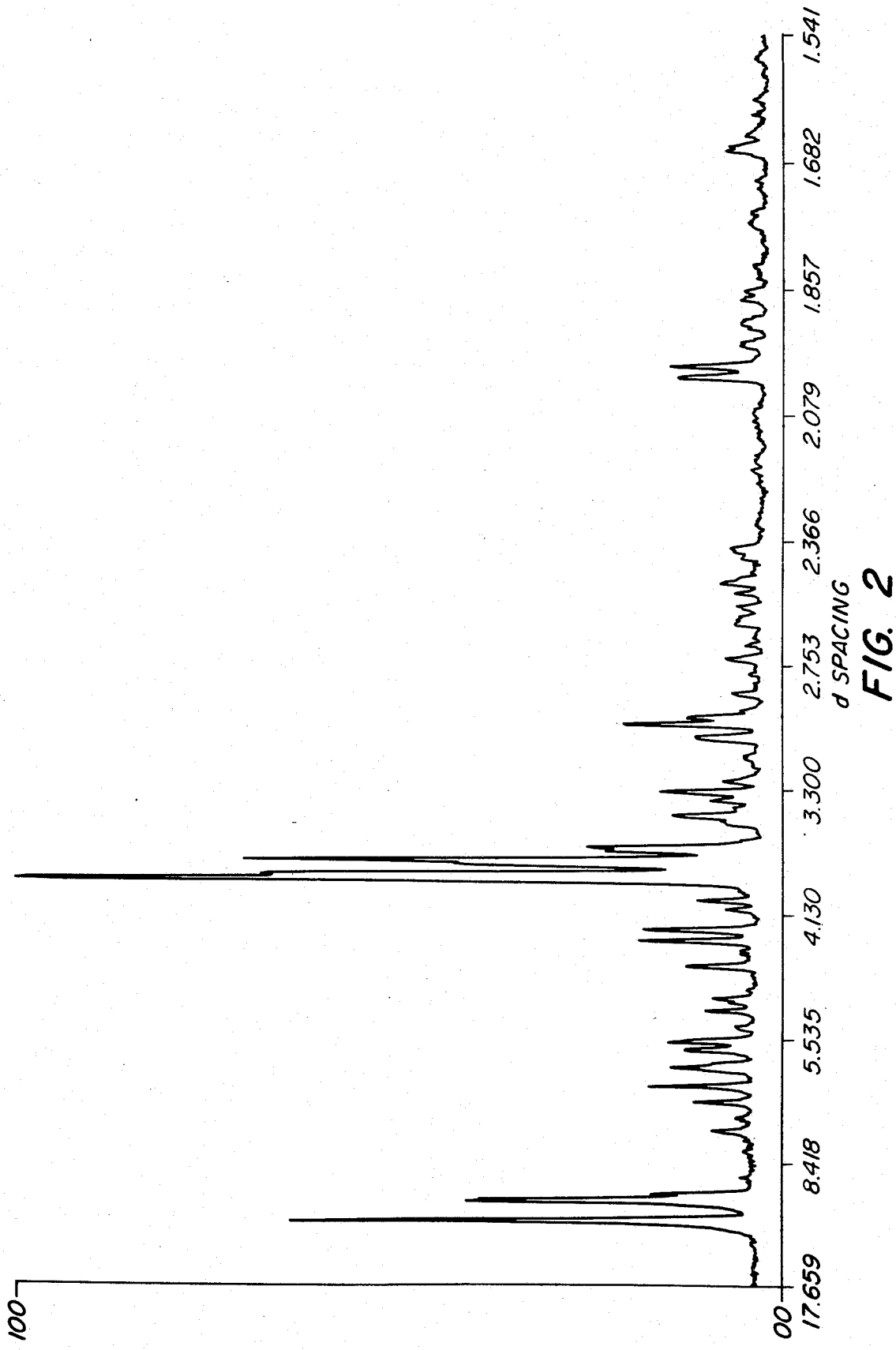
FIG. 2 is an X-ray diffraction pattern of a commercial Union Carbide Silicalite known as S-115.

Referring now to FIG. 2 herein, the X-ray powder diffraction of Silicalite (600° C. calcination in air for one hour) has as its four strongest lines (i.e. interplanar spacings) those at the d values listed in Table II.

In FIG. 3, the X-ray powder diffraction is shown of Silicalite with magnesium acetate added following U.S. Pat. No. 4,283,306, Example 82. The purpose of the magnesium acetate addition is the promotion of the crystalline silica. As expected from prior art, the fundamental X-ray powder diffraction pattern is unchanged by the addition of the magnesium promoter. However, a peak at d (2.10 Å) is identified as magnesium oxide showing that a mixture of separate phases of Silicalite and magnesium oxide results from preparation of magnesium promoted Silicalite following prior art teachings. See Table III herein.

In contrast, the crystalline magnesium silicate disclosed in our invention is a new material with a unique and heretofore undisclosed structure. No evidence of an admixture of two phases is found.

In FIG. 4, which is the X-ray diffraction pattern of material of our invention made by Example 2, it is sharply differentiated from the Silicalite and ZSM-5 by its unique pattern. The strongest lines (i.e. (interplanar spacings) of the X-ray diffraction pattern are essentially the same as the material made by Example 1, i.e. as recited in Table I. Lines at d (Å) 4.08 and 3.38 are the strongest whereas these are very weak or non-existent in the prior art Silicalite and ZSM-5. A further distinction may be seen by reference to the strongest lines of Silicalite and ZSM-5 of d (Å) 11.04 and 9.92 (see Table II) which are moderate to weak in the X-ray pattern of our crystalline magnesium silicate and in reverse order of intensity.

At levels up to 12 wt. % magnesia (MgO), there is no evidence of a crystalline phase of MgO (periclase) in the X-ray pattern. This contrasts with the pattern of Silicalite having been MgO promoted shown in FIG. 2 prepared according to the teachings of U.S. Pat. No. 4,283,306.

Our material has also been analyzed by scanning electron microscopy. A continuing problem associated with prior art methods of promotion of the crystalline silica with magnesium is the lack of uniformity on a molecular level of such mixtures. In a Scanning Electron Microscope examination of our new crystalline magnesium silicate, the Scanning Electron Microscope pattern shows a highly uniform magnesium to silica distribution indicative of material of our invention. Microtome slicing of particles prepared by Example 82 shows that the magnesium as expected is adhering to the outside surfaces of the crystalline silica. However, our invention crystalline magnesium silicate when similarly examined shows uniform distribution throughout the particle including inside the channels and cavities of the crystalline magnesium silicate. We believe its extraordinarily uniform distribution of magnesium throughout the catalyst is due to the method of preparation in which the magnesium is added to the original mixture before crystallization takes place.

Our final preferred composition is, by weight, about 91-98% $SiO_2$, and 2-9% MgO. The new crystalline magnesium silicate described herein is substantially free of alumina but may contain very minor amounts of aluminum attributable primarily to the presence of aluminum impurities in the reactants and/or equipment employed.

The ingredients of our preferred crystalline magnesium silicate are sodium silicate (which may normally contain about 150 to 300 ppm alumina as an impurity in the sodium silicate solution), magnesium chloride, tetrapropyl ammonium bromide, sodium chloride, and water. Two solutions are formed. One solution comprises about 6 to about 7 mole percent alkali metal halide, about 0.1 to about 0.45 mole percent magnesium salt and the balance to 100% deionized water. The other solution is a sodium silicate solution comprising about 1 to about 2 mole percent $Na_2O$ and about 4-5 mole percent $SiO_2$, with the balance to 100 mole percent water. Equal weights of the two solutions are poured together to make a reaction mixture which forms a precipitate and is stirred. It is then maintained between about 175° C. and 195° C. for about two to five days to form a solid dry product, and thereafter calcined, preferably at between 550° C. to 580° C. for about 4 to about 16 hours. After calcination, the magnesium silicate is washed with a 5% $NH_4Cl$ aqueous solution for approximately 90 minutes until essentially sodium free. The ion exchange leaves the crystalline magnesium silicate in the ammonium form which can be thermally decomposed to the hydrogen form.

A templating material of a composition described elsewhere herein may be incorporated in the first solution described above. A concentration of about 0.44 to about 0.48 mole percent templating material will impart desirable shape- and size-selectivity as demonstrated in Examples 7, 8, 10, and 11 and Tables IV and V and elsewhere herein.

Any magnesium salt of good aqueous solubility may be used. Examples of suitable inorganic salts include magnesium chloride, bromide or other halide in hydrated form; magnesium nitrate, chlorate, perchlorate or orthophosphate. Examples of suitable organic salts include magnesium acetate, formate, oxalate or benzoate. As known in the art, a wide variety of alkali metal silicate solutions are available commercially, and we may choose any such pre-dissolved solution to achieve the desired ratios of $Na_2O$, $SiO_2$, and other components recited herein.

Thus a typical recipe following the above steps and physical parameters would react a solution (A) of about 92.8 mole percent deionized water, about 0.11-0.43 mole percent $MgCl_2.6H_2O$, about 0.46 mole percent tetrapropyl ammonium bromide template, and about 6.3% sodium chloride with an equal amount of solution (B) of about 1.3 mole percent sodium oxide and 4.4 mole percent silicon dioxide in about 94.3 mole percent water.

The amounts of the two solutions, while nominally equal, can in practice vary somewhat from equality bearing in mind above all the overall ratio of magnesium to silica desired for the final product, as stated elsewhere herein.

The structure of the product of the synthesis is related in part to the molar ratio of $SiO_2$ to $R_4N$ used in the preparation. When this ratio is infinite (no $R_4N$ added) only two principal lines in the X-ray powder diffraction are obtained at a d (interplanar spacing) of 4.08 Å and 3.4 Å. At a molar ratio of $R_4N$ to $SiO_2$ of 0.33 or above, the principal lines in the X-ray powder diffraction pattern are at a d (interplanar spacing) of 3.85 Å, 3.80 Å, 3.71 Å, and 11.1 Å. Within the preferred range of a $R_4N$ to $SiO_2$ molar ratio of 0.1 to 0.15 the X-ray powder diffraction shows a d (interplanar spacing) as given in Table I.

The molar ratio of magnesia to silica is critical to the development of the proper powder X-ray diffraction pattern defining the crystalline magnesium silicate of this invention. At a molar ratio of magnesia to silica above 0.25 the powder X-ray pattern defining the crystalline magnesium silicate will not reveal the characteristic d (interplanar spacing) of Table I. The principal lines obtained with material of molar ratio of magnesia to silica above 0.25 are at d (interplanar spacing) of 3.83 Å, 11.05 Å, 3.78 Å and 9.92 Å.

Reactants may fall within the following ranges:

| Reactants | Broad | Preferred |
|---|---|---|
| $Na_2O/SiO_2$ | 0.01–15.0 | 0.5–10.0 |
| $MgO/SiO_2$ | 0.005–0.25 | 0.025–0.15 |
| $R_4N^+/SiO_2$ | 0.05–0.2 | 0.1–0.15 |
| $H_2O/SiO_2$ | 10–100 | 25–50 |

A preferred "basic formula" is as follows:

Basic Formula (I) 181.4 g "N" Sodium Silicate { 52.1 g $SiO_2$ / 16.1 g $Na_2O$ / 113.2 g $H_2O$
224.1 g Deionized $H_2O$ (II)
310.1 g Deionized $H_2O$
23.4 g Tetrapropyl Ammonium Bromide
17.6 g Magnesium Chloride.$6H_2O$
68.2 g Sodium Chloride Total Synthate 647.4 g $H_2O$
68.2 g NaCl
52.1 g $SiO^2$
23.4 g TPABr
17.6 g $MgCl_2.6H_2O$
16.1 g $Na_2O$ As template, i.e. compositions which influence the size and shape of pore formation during crystallization, we may use any of the following:
(1) Water-soluble quaternary ammonium salts of the general formula:

$R_4N^+X^-$ where R is an alkyl group of 1-6 carbon atoms and X is $Cl^-$, $Br^-$, $I^-$, or $OH^-$, such as:

| | |
|---|---|
| Tetrapropyl ammonium bromide | (n-propyl or isopropyl) |
| Tetrapropyl ammonium chloride | |
| Tetrapropyl ammonium iodide | |
| Tetrapropyl ammonium hydroxide | |
| Tetraethyl ammonium bromide | |
| Tetraethyl ammonium chloride | |
| Tetraethyl ammonium iodide | |
| Tetraethyl ammonium hydroxide | |
| Tetrabutyl ammonium bromide | (n-butyl, isobutyl, tertial butyl) |
| Tetrabutyl ammonium chloride | |
| Tetrabutyl ammonium iodide | |
| Tetrabutyl ammonium hydroxide | |

Also: tetramethyl ammonium, tetrapentyl ammonium, tetrahexyl ammonium halides.
Other organic nitrogen compounds, i.e. mono, di and trialkyl amines, aniline, pyrolidine, ethylene diamine.
(2) Quaternary ammonium salts—tetraalkyl ammonium hydroxides:
  Tetrapropyl ammonium hydroxide TPAOH
  Tetraethyl ammonium hydroxide TEAOH
  Tetrabutyl ammonium hydroxide TBAOH
  Tetramethyl ammonium hydroxide TMAOH
Similar nitrogen-containing organic compounds may be substituted.

Specific examples of the manufacture of our new catalyst are shown in Examples 1, 2, 3, and 6.

EXAMPLE 1

181.84 grams of "N" brand sodium silicate was mixed with 227.1 g of deionized water to form solution I. To 310.23 g of deionized water was added 22.79 g tetrapropyl ammonium bromide, 7.61 g magnesium chloride hexahydrate, and 68.55 g sodium chloride. This solution was mixed simultaneously with solution I in another bearer. The resultant precipitate was dispersed with a laboratory stirrer to a fluid, milky slurry, and mixed well for 15 minutes. The slurry was placed in a 600 ml Teflon sleeve in a Parr autoclave at 187° C. for 68 hours, and allowed to crystallize under autogeneous pressure. The pH was 10.8.

After cooling to facilitate handling, the crystals were filtered from the mother liquor and washed thoroughly with deionized water. Drying and calcination were accomplished at 145° C. and 580° C., respectively, for 16 hours each.

The calcined material was subjected to a series of three ion exchange procedures with 0.093 molar aqueous ammonium chloride at 80°–90° C. for 90 minutes each contact period. After the third exchange the sample was washed with deionized water until the filtrate had a negative test for free chloride, with silver nitrate solution. After drying and recalcination at 550° C., the material was analyzed by X-ray diffraction using standard techniques. The resultant diffractogram is shown in FIG. 1 and reported in Table I.

EXAMPLE 2

Two separate reactant solutions were prepared according to the following formulae:
(1)
  184.34 g "N" sodium silicate—PQ Corp., Philadelphia, Pa.
  223.0 g deionized water
(2)
  310.32 g deionized water
  23.45 g tetrapropyl ammonium bromide
  17.37 g magnesium chloride hexahydrate 68.43 g sodium chloride.

After mixing each solution separately, they were combined simultaneously in a separate flask to form a thick precipitate. The precipitate was dispersed with stirring to form a slurry of pH=10.601. After mixing for 15 minutes, the slurry was immediately placed in a Teflon lined stainless steel autoclave. The crystallization was allowed to take place for 42 hours at 168° C., under autogeneous pressure. The crystals were separated from the mother liquor, and washed with deionized water. Drying was accomplished at 150° C. for 16 hours, followed by calcination at 550° C. for 16 hours. The X-ray diffraction for the calcined material is shown in FIG. 4, which was obtained by standard techniques.

Ion exchange, sodium for ammonium, was accomplished in three stages using 0.1 m aqueous ammonium chloride at 80°-90° C., for 60-90 minutes each contact period. The ammonium form of the crystalline material was washed with deionized water until no trace of chloride was detected with silver nitrate solution in the filtrate. The final H-form of the catalyst was obtained by calcining, after drying, at 500° C. for 16 hours. The material was stored in a sealed jar until an activity test could be performed.

EXAMPLE 3

A similar catalyst was prepared, utilizing magnesium acetate as the magnesium source. Solution I was prepared by diluting 181.7 g "N" sodium silicate with 224.1 g of deionized water, and mixing well.

Solution II was prepared by dissolving 23.2 g tetrapropyl ammonium bromide, 17.6 g magnesium acetate tetrahydrate (Aldrich), and 68.1 g sodium chloride in 310.4 g deionized water. Solutions I and II were mixed simultaneously to form a white precipitate, as before. The precipitate was dispersed by mixing for 10-15 minutes, and then placed in a Teflon lined Parr autoclave (pH=10.24). Crystallization was accomplished at 183° C. for 66 hours, and autogeneous pressure. After filtering and washing, the crystals were subjected to the ion exchange procedure with ammonium chloride as previously outlined. After washing, drying and calcining analysis by X-ray diffraction exhibited the same characteristic lines and relative intensities as set forth in Table I of the text.

EXAMPLE 4

Silicalite S-115, Union Carbide, lot #961882060006-S-14 was analyzed by X-ray diffraction. The pattern is shown in FIG. 2, and is essentially the same starting material identified in U.S. Pat. Nos. 4,061,724, and 4,283,306.

EXAMPLE 5

Example 82 of U.S. Pat. No. 4,283,306, assigned to DuPont, was then followed to prepare a magnesium containing catalyst used for selective alkylation of aromatic based hydrocarbons.

6.0 gm of the silica based material of Example 4 was mixed with a solution containing 5.25 gm magnesium acetate in 15 ml of deionized water. After drying at 120° C. for 3 days, the material was calcined at 250° C. for 3 hours, then at 580° C. for 16 hours. A similar X-ray diffraction pattern was obtained for the magnesium impregnated material, with one notable exception. A significant peak at d=2.1 appeared which is characteristic of periclase, a crystalline form of MgO. The pattern is shown in FIG. 3 and summarized in Table III. The sample was found to contain 13.6% MgO.

TABLE III

| XRD - Reproduction of example 82 of USP 4,283,306 | | |
|---|---|---|
| | D | Relative Intensity |
| 1. | 3.84 | 100.00 |
| 2. | 11.11 | 66.71 |
| 3. | 3.71 | 53.48 |
| 4. | 3.80 | 45.86 |
| 5. | 9.98 | 34.98 |
| 6. | 3.75 | 27.87 |
| 7. | 3.65 | 17.87 |
| 8. | 2.10 | 16.16 |
| 9. | 2.98 | 14.16 |
| 10. | 6.34 | 12.52 |
| 11. | 5.98 | 12.42 |
| 12. | 4.25 | 11.80 |
| 13. | 5.56 | 10.86 |
| 14. | 9.65 | 10.68 |
| 15. | 4.34 | 10.03 |
| 16. | 2.01 | 9.45 |
| 17. | 3.29 | 9.42 |
| 18. | 3.43 | 8.86 |
| 19. | 4.60 | 8.15 |
| 20. | 5.69 | 8.08 |

EXAMPLE 6

A crystalline catalyst was prepared by first mixing 182.1 g of "N" brand sodium silicate solution with 224.2 g of deionized water. This is designated solution I. Solution II was prepared by dissolving 22.7 g tetrapropyl ammonium bromide, 17.2 g magnesium chloride hexahydrate, and 68.5 g sodium chloride in 310.8 g of deionized water. After dissolution was complete, solution I and solution II were mixed simultaneously in a third flask. The resultant, white gel-like precipitate was dispersed with the help of an electric laboratory paddle stirrer and mixed for 10-15 minutes. The slurry obtained had a pH=10.45, and was immediately placed in a Teflon sleeved Parr autoclave. The slurry was allowed to crystallize, without agitation, at 180°-185° C. for three days under autogeneous pressure.

After three days the material was removed from the autoclave, filtered and washed with approximately 10 L. of deionized water. The filter cake was dried at 140° C. for 16 hours, and calcined at 550°-580° C. for 16 hours. Approximately 40 grams of material is obtained.

In order to remove sodium, undesirable for catalytic applications, the calcined material is subjected to a series of three washes with 5% by weight aqueous ammonium chloride at 80°-90° C. for 90 minutes each. The ammonium form of the crystalline material was washed with deionized water, until no free chloride can be detected with 1.0N silver nitrate added dropwise to the filtrate. The washed filter cake was again dried at 140° C. for 16 hours, and calcined for 16 hours at 550°-580° C. A sample of this material was analyzed with standard powder X-ray diffraction techniques, utilizing copper Ka radiation. The pattern was very similar to that of FIG. 1. Analysis of this material gave 8.6% magnesium as MgO, and 940 ppm $Al_2O_3$ impurity.

As indicated previously, our invention includes the use of our new catalyst for the alkylation of aromatics. The alkylation reactions may be conducted in batch or continuous fashion. The aromatics we may employ include the single-ring aromatics, or mono-aromatics, such as benzene, toluene, or phenol. Substitutions on the ring at the meta and ortho positions prior to alkylation by our method will not inhibit the reaction itself, but the advantages of our invention are much more apparent with materials which will yield the attachment of a relatively simple alkyl or alcohol group in the para position with respect to a subsisting group (such as in the use of phenol and toluene), since the "molecular sieve" function of our catalyst, when its pore size has been controlled in the manner described, will selectively yield compounds having a para orientation. Specifically, we prefer to use as alkylating agents olefins and monoalcohols having 1-3 carbon atoms, i.e. methanol, ethanol, propanol, isopropanol, propylene, and ethylene. The term "alkylating conditions" as used herein includes temperatures between about 300°-500° C., pressures greater than atmospheric but less than 350 psig, molar ratios of alkylating agent to aromatic in the range of about 0.2-1.0:1, and feed rates of about 0.5 to 10 grams of feed mixture per gram of catalyst per hour. These conditions generally will effect alkylation with or without pore selectivity capability, and may be varied as is known to workers skilled in the art to affect conversion rates, times, selectivity, and other factors.

EXAMPLE 7

Alkylation of Toluene with Ethylene

Approximately 1.0 gm of the crystalline magnesium silicate catalyst prepared as in Example 1 was placed in a 0.25″ OD SS316 tube, and held in place with a combination of wire screen and glass wool. Reagent grade toluene was vaporized in a carefully metered gas stream composed of nitrogen and ethylene, at a WHSV of 1.0 gm of Toluene/gm. catalyst/hr. The ratio of aromatic to alkylating agent was contolled at 1.8:1.0. Both feed and reactor effluent were measured with an on-line gas chromatograph. The reaction temperature was maintained at 400° C. in an agitated molten lead bath. At an inlet pressure of 1 atm, the condensible reaction products were collected over a 16-hour period and analyzed for conversion and selectivity to p-ethyl toluene. Toluene conversion was 51.6%, and 78.5% of the ethyl toluenes was p-ethyl toluene. Yield loss due to disproportionation or transalkylation accounted for about 1.6% of the liquid product.

At 425° C., and similar feed rates and conditions, toluene conversion was observed to be 49.2%, and p-ethyl toluene was 80.1% of the total ethyl toluene fraction; o-ethyl toluene was less than 0.1% of the product collected.

EXAMPLE 8

A magnesium silicate catalyst prepared according to Example 6 was tested in a similar manner for the vapor phase alkylation of toluene with ethylene at 400° C., and atmospheric pressure. At a toluene to ethylene molar ratio of 2.3:1.0, and a WHSV of about 1.0 gm toluene/gm catalyst/hr using nitrogen as a diluent, a condensed product was collected overnight, 16 hours, and analyzed by GC. Conversion was observed to be 85% of theoretical with a 93.7% selectivity to p-ethyl toluene; side reactions accounted for 1.9% of the product analyzed. Yield loss to benzene, ethylbenzene and polysubstituted aromatic was predominant, with little evidence of ethylene oligimerization present.

EXAMPLE 9

Comparative

The catalyst samples as described in Examples 4 and 5 were also tested for activity and selectivity in the vapor phase alkylation of toluene with ethylene to produce p-ethyl toluene. At a WHSV of 1.0-1.2g toluene/gm catalyst/hr and a toluene:ethylene molar ratio of 2.5-2.8:1.0 the liquid product was collected over an 8-16 hour period for each of the reaction temperatures 400° C. and

|  | % Toluene Converted | % p-ethyl toluene in Ethyl Toluenes | % Side Products |
|---|---|---|---|
| 400° C. | | | |
| Silicalite (Ex. 4) | 48.4% | 56.0% | 6.4% |
| Silicalite/MgO (Ex. 5) | 41.3% | 91.7% | 3.6% |
| 475° C. | | | |
| Silicalite (Ex. 4) | 37.6% | 25.0% | 24.4% |
| Silicalite/MgO (Ex. 5) | 67.2% | 78.9% | 16.6% |

EXAMPLE 10

Benzene Alkylation with Isopropanol (IPA)

A 1-inch OD stainless steel tubular reactor, 20 inches long was loaded with 21.2g of 1/16″ by ¼″ extrudates of the magnesium silicate catalyst prepared according to Example 6. Catapal SB alumina at a level of 15% w/w was used as a binder. A 2:1 molar mixture of benzene and isopropanol was fed into the top of the tubular reactor which was loaded with an inert ceramic to act as a preheating section, prior to the catalyst bed. Initial reaction conditions were 375° C. with a back pressure of 100 psig, and a liquid feed flowrate of 10 ml/min. After two days of operation, liquid product was collected over a 5-hour period and analyzed for cumene. 40.4% of the IPA was converted to cumene, with about 10.9% converted to di- and tri-isopropyl benzenes. After 168 hours of operation, no significant loss of catalytic activity was observable.

EXAMPLE 11

Phenol Alkylation with Methanol

Phenol and methanol were separately vaporized in a controlled flow of nitrogen, mixed, then passed over a sample of the magnesium silicate catalyst prepared in Example 1. At a WHSV of 0.5 gm of liquid feed (methanol + phenol) per gram of catalyst per hour and a reaction temperature of 350° C., a condensed liquid product was collected over a sixteen-hour period and analyzed by capillary GC. A derivitization method employing the trimethyl silyl ethers of the o-p-m cresols was used to determine their relative concentrations. The anaylsis is tabulated below, on a water free basis:

| Methanol | 12.1% |
|---|---|
| Phenol | 70.8% |
| Anisole | 1.9 |
| o-Cresol | 6.7 |
| m-cresol | 0.23 |
| p-cresol | 2.1 |
| Xylenols + heavies | 6.2 |

Table IV compares the ability of our molecular sieve catalyst to add an ethylene group, in the desired para-configuration, to toluene with that of other materials commonly used for the purpose. In this set of comparisons, the procedure was similar to that of Example 7.

TABLE IV

Toluene Alkylation Data

| Catalyst | % Theoretical Conv. of C₂H₄ | Wt. % P—ethyl Toluene in Ethyl Toluenes | Wt. % Others - Xylene, Benzene, Trimethyl Benzene |
|---|---|---|---|
| Silicalite S-115 | 88.9% | 57% | 6.4% others |
| HZSM-5* | 86.0% | 46% | 6.3% others |
| Magnesium Silicate | 92.0% | 82% | 2.2% others |

Tr = 400° C., P = 1-2 atm. WHSV = 1.0 g Toluene/g-cat/hr
Toluene: C₂H₄ = 1.8-2.5:1 molar
*Prepared according to U.S. Pat. No. 3,702,886.

From Table IV, it may be seen that our material is not only more efficient in conversion, but exhibits a significant reduction in "others" along with a much higher ratio of p-ethyl toluene to other ethyl-toluenes. Our catalyst is particularly useful for alkylating materials of the formula AR where A is a benzene ring and R is hydrogen, hydroxyl or methyl, i.e. benzene, phenol, and toluene. The alkylation is most conveniently performed with methyl or ethyl groups.

Comparable results are seen in Table V. on benzene alkylation with isopropanol to yield cumene. The procedure again was similar to that of Example 7.

TABLE V

Benzene Alkylation Data

| Catalyst | Wt. % Cumene in Product | % Theoretical Conv. of Isopropanol | Wt. % Other Alkyl Benezenes |
|---|---|---|---|
| HZSM-5* | 27.3 | 53.0 | 13.2 |
| Magnesium Silicate | 25.3 | 48.0 | 5.2 |

Tr = 350-375° C., P = 100 psig, Benzene:Isopropanol = 2:1
WHSV = 2.4 g Feed/g cat/hr
*Prepared according to U.S. Pat. No. 3,702,886.

Again, the "percent others" is less than half that of the conventional materials.

The crystalline magnesium silicates can be used either in the alkali metal form, the ammonium form or the hydrogen form. They can also be used in combination with hydrogenation catalyst components such as Group VIB (chromium, molybdenum, tungsten) as well as Group VIII (iron, cobalt, nickel) or a noble metal such as platinum, palladium, and rhodium. Such components can be impregnated on or physically intimately admixed with the cystalline magnesium silicate.

The crystalline magnesium silicate when used as an absorbent or catalyst should preferably be converted to the dehydrated form by heating to a temperature in the range of 200° to 600° C. in an atmosphere such as air, nitrogen, etc., and at atmospheric or subatmospheric pressure for between 1 to 24 hours.

We claim:

1. Method of making a magnesium-containing silica composition consisting essentially of
   (1) forming an aqueous reaction mixture consisting essentially of about 0.05 to about 0.225 mole % magnesium salt, about 0.22 to about 0.24 mole % tetrapropyl ammonium halide templating material, about 0.5 to 1 mole % alkali metal oxide, about 2 to 2.5 mole % SiO₂ and about 3 to about 3.5 mole % alakli metal halide, in deionized water to form 100 mole %, in a container to form a precipitate,
   (2) stirring the reaction mixture of step (1) and heating it at a temperature of about 175° C. to about 195° C. to form a crystallized product, and
   (3) calcining the product of step (2).

2. Method of claim 1 wherein the templating material is tetrapropyl ammonium bromide.

3. Method of claim 1 followed by an ion exchange step comprising contacting the composition so made with an ammonium salt solution.

4. Crystalline magnesia-silica composition made by a process of claim 1 having a molar ratio of MgO:SiO₂ of 0.005–0.25 and X-ray diffraction peaks at d=4.08±0.07, 3.38±0.05, 10.08±0.2, 3.87±0.07, 2.48±0.05, 11.2±0.2 and 3.83±0.07.

5. A calcined crystalline magnesia-silica composition having a molar ratio of MgO:SiO₂ of 0.005–0.25 and X-ray diffraction peaks at d=4.08±0.07, 3.38±0.05, 10.08±0.2, 3.87±0.07, 2.48±0.05, 11.2±0.2 and 3.83±0.07.

6. A calcined magnesia-silica composition of claim 5 having the X-ray diffraction pattern of FIG. 1.

7. A calcined magnesia-silica composition of claim 5 having the X-ray diffraction pattern of FIG. 4.

8. A calcined magnesia-silica composition of claim 5 wherein the molar ratio of MgO:SiO₂ is 0.025 to 0.15.

* * * * *